(12) United States Patent
Shimoe et al.

(10) Patent No.: US 6,464,678 B2
(45) Date of Patent: Oct. 15, 2002

(54) DISPOSABLE DIAPER

(75) Inventors: Nariaki Shimoe, Kagawa-ken (JP); Toru Sasaki, Kagawa-ken (JP); Yoshinori Kumasaka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 10 days.

(21) Appl. No.: 09/754,655

(22) Filed: Jan. 4, 2001

(65) Prior Publication Data

US 2001/0007936 A1 Jul. 12, 2001

(30) Foreign Application Priority Data

Jan. 6, 2000 (JP) ........................................ 2000-000855

(51) Int. Cl.[7] .............................................. A61F 13/15
(52) U.S. Cl. ........................ 604/385.27; 604/385.04; 604/385.18; 604/385.28; 604/386
(58) Field of Search .................. 604/385.04, 385.18, 604/385.27, 385.28, 386

(56) References Cited

U.S. PATENT DOCUMENTS 5,197,959 A   3/1993  Buell
5,593,400 A   1/1997  O'Leary
5,624,424 A * 4/1997  Saisaka ................. 604/385.02
5,855,573 A   1/1999  Johansson

FOREIGN PATENT DOCUMENTS

| EP | 0 309 246 A1 | 3/1989 |
| EP | 0 450 541 A2 | 10/1991 |
| EP | 0 953 325 A2 | 11/1999 |
| EP | 0 953 326 A2 | 11/1999 |
| JP | 11-188056 | 7/1999 |
| WO | WO 99/25289 | 5/1999 |

* cited by examiner

Primary Examiner—Rodney M. Lindsey
Assistant Examiner—Angela J Grayson
(74) Attorney, Agent, or Firm—Baker & Daniels

(57) ABSTRACT

A disposable diaper that includes a topsheet, a backsheet and a core disposed therebetween to define a front waist region, a rear waist region and a crotch region extending therebetween. A first elastic member extends longitudinally of the diaper across a middle zone of the core between the front and rear waist regions and is disposed between the backsheet and the core and secured to the backsheet. Second elastic members extend longitudinally of the diaper across the transversely opposite side zones of the core between the front and rear waist regions and are disposed between the backsheet and the core and bonded to the backsheet.

4 Claims, 2 Drawing Sheets

DISPOSABLE DIAPER

BACKGROUND OF THE INVENTION

This invention relates to a disposable diaper for absorption and containment of body fluids discharged thereon.

Japanese Patent Application Disclosure No. 1999-188056 describes a disposable diaper comprising a liquid-pervious topsheet, a liquid-impervious backsheet and a liquid-absorbent core disposed between these two sheets. Configurationally, this diaper of prior art comprises, as viewed in its longitudinal direction, a front waist region, a rear waist region and a crotch region extending between these front and rear waist regions. In the foregoing Disclosure, the diaper is described to be characterized in that there is provided an elastic member extending across a middle zone of the core in the longitudinal direction between the front and rear waist regions. This elastic member is disposed between the backsheet and the core and secured under tension to the backsheet. In the crotch region of the diaper, a tensile force of the elastic member biases the middle zone of the core to rise against a wearer's crotch with transversely opposite side zones of the core except the middle zone remaining in a slackened state. Thus the crotch region presents its cross-section of an inverted V-shape so that the core may have its transverse dimension in the crotch region substantially reduced. In this way, any remarkably irregular deformation of the crotch region can be avoided and an efficient absorption of body fluids into the core can be ensured even when the crotch region of the diaper put on the wearer's body is tightly held between the wearer's thighs.

With the diaper described in the foregoing Disclosure, the transversely opposite side zones of the core are not biased by the elastic member to rise and therefore the body fluids discharged on the diaper tend to flow down from the middle zone toward the side zones of the core. The amount of body fluids having reached the side zones of the core may leak sideways out from the crotch region. Certainly, the diaper described in the foregoing Disclosure is provided in the vicinity of the side zones of the core with leak-barrier cuffs as barriers against such leak of body fluids. However, so far as the transversely opposite side zones of the core are not biased by the elastic member to rise, it is apprehended that free side edges of the respective cuffs might improperly rise, i.e., slant or collapse outward laterally of the diaper as the diaper is put on the wearer's body. Consequently, there is an apprehension that the leak-barrier cuffs could not fulfill their desired function.

SUMMARY OF THE INVENTION

It is an object of this invention to provide a disposable diaper improved so that the transversely opposite side zones of the core are not slackened downward even when the middle zone of the core rises under the tensile force of the elastic member extending in the longitudinal direction between the front and rear waist regions and thereby any sideway leakage of body fluids can be reliably prevented.

According to this invention, there is provided a disposable diaper comprising a liquid-pervious topsheet, a liquid-impervious backsheet and a liquid-absorbent core disposed between the topsheet and the backsheet to define a front waist region, a rear waist region and a crotch region extending between the front and rear waist regions, the diaper further comprising a first elastically stretchable member lying in a middle zone of the core and extending longitudinally of the diaper between the front and rear waist regions and being disposed between the backsheet and the core and secured under tension to the backsheet, and a pair of second elastically stretchable members which lie in transversely opposite side zones of the core and extending longitudinally of the diaper between the front and rear waist regions are disposed between the backsheet and the core and secured under tension to the backsheet.

The disposable diaper according to this invention has the crotch region adapted to be curved with the W-shaped cross-section and thereby to have its transverse dimension substantially reduced so that any irregular deformation of the crotch region may be reliably avoided even when the crotch region of the diaper put on the wearer's body is tightly held between the wearer's thighs.

The transversely opposite side zones of the core are not slackened downwardly of the diaper but lifted upwardly of the diaper under the tensile force of the second elastic members generated as these elastic members are stretched as the diaper is put on the wearer's body. In this way, the side zones of the core form the barriers against the discharged body fluids and reliably prevent the body fluids from leaking sideways.

In the case of the diaper provided with the leak-barrier cuffs, the fixed side edge portions of the respective cuffs lie in the vicinity of the side zones of the core lifted up under the tensile force of the second elastic members. This unique placement ensures that the free side edge portions of the cuffs can be erected in postures substantially vertical or slightly slanted inward laterally of the diaper. In this way, the free side edge portions of the cuffs can be prevented from collapsing outwardly of the diaper. The free side edge portions of the cuffs are adapted to be erected around lines defined in the vicinity of the side zones of the core. This means that the cuffs will be able to fulfill their leak-barrier function even when the cuffs are of the arrangement in which a distance between the fixed side edge portion and the associated free side edge portion is relatively small.

DETAILED DESCRIPTION OF THE PREFERRED EMBODIMENTS

Details of a disposable diaper according to this invention will be more fully understood from the description given hereunder with reference to the accompanying drawings.

Figure 1:
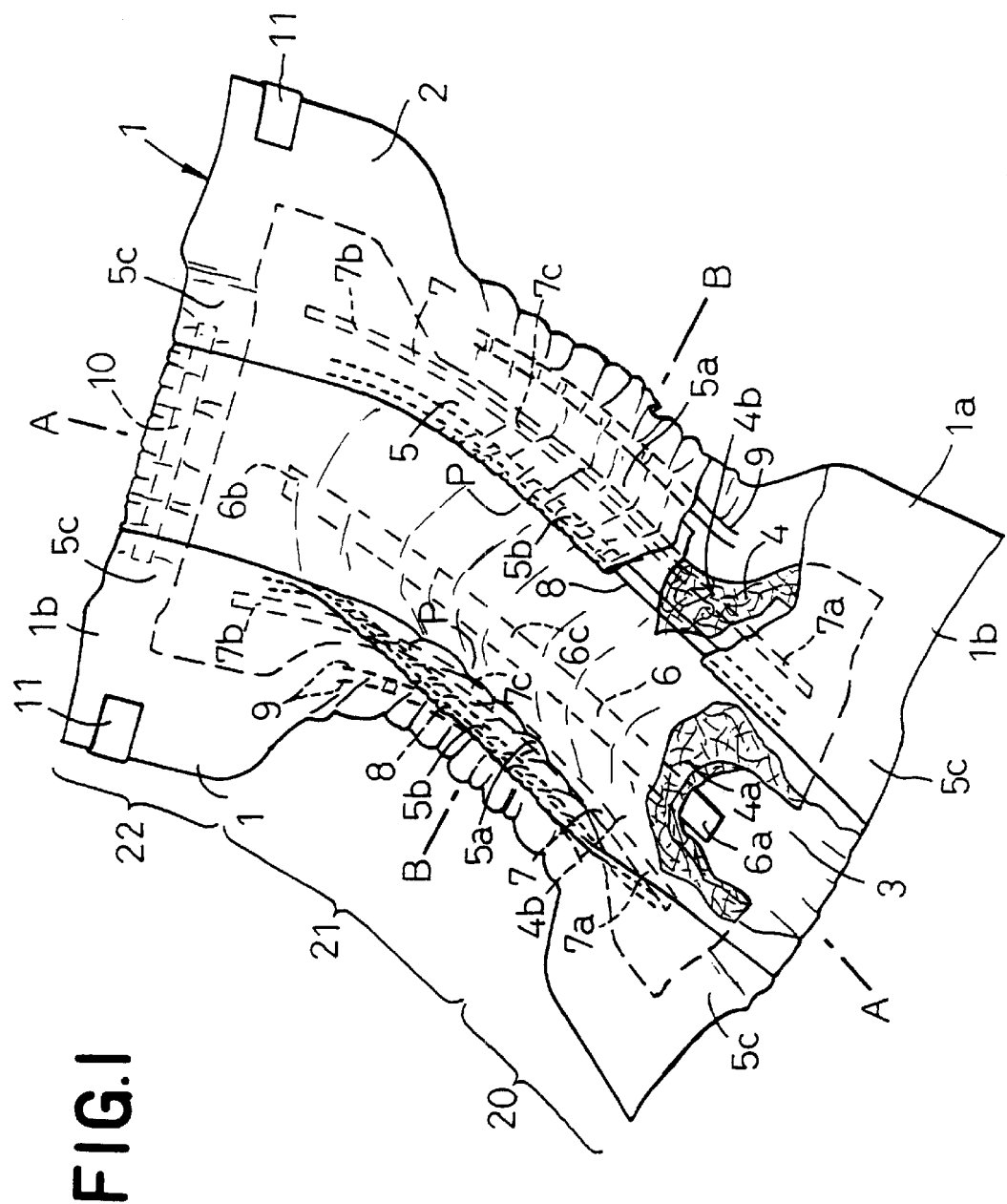
FIG. 1 is a perspective view showing one embodiment of a partially cutaway disposable diaper according to this invention.
Figure 2:
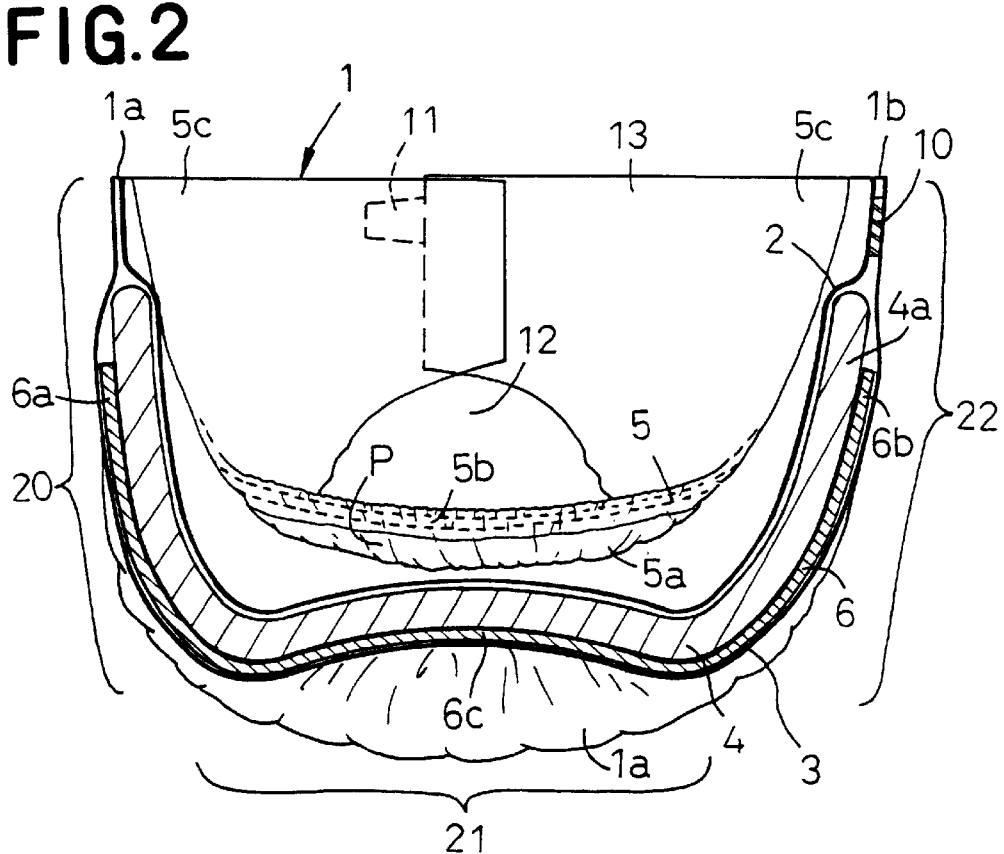
FIG. 2 is a sectional view taken along line A—A in FIG. 1.

FIG. 1 is a perspective view depicting one embodiment of a partially cutaway disposable diaper 1 according to this invention and FIG. 2 is a sectional view taken along line A—A in FIG. 1 depicting the diaper 1 as put on a wearer's body. The diaper 1 basically comprises a liquid-pervious topsheet 2, a liquid-impervious backsheet 3 and a mat-like liquid-absorbent core 4 disposed between these sheets 2, 3 and bonded to the inner surface of at least one of these sheets 2, 3. The diaper 1 is longitudinally configured by a front waist region 20, a rear waist region 22 and a crotch region 21 extending between the front and rear waist regions 20, 22. The diaper is contoured by transversely opposite side edges 1a extending in parallel to each other longitudinally of the diaper 1 and curving in the crotch region inwardly of the diaper 1 to describe circular arcs and longitudinally opposite ends 1b extending in parallel to each other transversely of the diaper 1. The diaper 1 is provided with a pair of leak-barrier cuffs 5 lying in vicinity of transversely opposite side zones 4b of the core 4 and extending longitudinally of the diaper 1.

The diaper 1 is further provided between the front waist region 20 and the rear waist region 22 with a single first elastically stretchable member 6 extending across a middle zone 4a of the core 4 and a pair of second elastically stretchable members 7 extending across the transversely opposite side zones 4b longitudinally of the diaper 1, respectively.

The first elastic member 6 has a front end portion 6a lying in the front waist region 20, a rear end portion 6b lying in the rear waist region 22 and a middle zone 6c lying in the crotch region 21. The first elastic member 6 is disposed between the backsheet 3 and the core 4 and has its front and rear end portions 6a, 6b secured under tension longitudinally of the diaper 1 to the backsheet 3. The middle zone 6c of the first elastic member 6 is secured neither to the backsheet 3 nor to the core 4.

Each of the second elastic members 7 has a front end portion 7a lying on the front waist region 20, a rear end portion 7b lying in the rear waist region 22 and a middle zone 7c lying in the crotch region 21. These second elastic members 7 are disposed between the backsheet 3 and the core 4 and have their front end portions 7a and the rear end portions 7b secured under tension longitudinally of the diaper 1 to the backsheet 3. The respective middle zone 7c of the these second elastic members 7 are bonded neither to the backsheet 3 nor to the core 4.

Each of the leak-barrier cuffs 5 has a fixed side edge portion 5a extending longitudinally of the diaper 1 in the vicinity of the associated side zone 4b of the core 4 and bonded to the upper surface of the topsheet 2, a free side edge portion 5b lying in the crotch region and extending inward transversely of the diaper 1 normally under an effect biasing this free side edge portion 5b to rise on the diaper 1, and longitudinally opposite fixed ends 5c lying in the front and rear waist regions 20, 22, respectively, and bonded to the upper surface of the topsheet 2 so that the end 5c may be fixedly collapsed inward laterally of the diaper 1. Elastically stretchable members 8 are secured under tension to the leak-barrier cuffs 5 so that these elastic members 8 may extend longitudinally of the diaper 1 along the respective free side edge portions 5b and be covered with parts of the respective free side edge portions 5b.

The diaper 1 is provided along its transversely opposite side edges 1a with a pair of elastically stretchable members 9 extending longitudinally of the diaper 1 to be associated with respective leg-holes 12. Each of these elastically stretchable members 9 is disposed between the associated side portion of the backsheet 3 and the side portion of the associated cuff 5 extending outward from its fixed side edge portion 5a laterally of the diaper 1 and secured under tension to the inner surface of at least one of said side portion of the backsheet 3 and the side portion of the associated cuff 5.

The diaper 1 is provided along the end 1b of the rear waist region 22 with film-like elastic member 10 associated with the waist-hole 13 extending transversely of the diaper 1. This elastic member 10 is disposed between the top- and backsheets 2, 3 and secured under tension to the inner surface of at least one of these two sheets 2, 3. The rear waist region 22 of the diaper 1 is provided with a pair of tape fasteners 11 having their proximal ends attached to the respective side edges 1a, respectively, so that these tape fasteners 11 extend inward laterally of the diaper 1. In the front waist region 20 of the diaper 1, a rectangular strip of target tape (not shown) is attached to the outer surface of the backsheet 3 so that the tape fasteners 11 may be anchored on the strip of target tape.

Along the transversely opposite side edges 1a of the diaper 1, the transversely opposite side portions of the topsheet 2 terminate immediately outside the transversely opposite side portions 4b of the core 4. The transversely opposite side portions of the backsheet 3 as well as the transversely opposite side portions of the cuffs 5 extend outward beyond the transversely opposite side portions of the topsheet 2 laterally of the diaper 1. The transversely opposite side portions of the top- and backsheets 2, 3 as well as of the cuffs 5 are bonded together as they are placed one upon another.

Referring to FIG. 1, gathers are formed along the transversely opposite side edges 1a, the longitudinally opposite ends 1b and the free side edge portions 5b of the cuffs 5 as the elastic members 9 associated with the leg-holes 12, the elastic member 10 associated with a waist-hole 13 and the elastic members 8 attached to the respective free side edge portions 5b of the cuffs 5 are relieved of tension. As shown, the diaper 1 is curved longitudinally thereof with its inner surface inside and contraction of the elastic members 8 attached to the free side edge portions 5b of the cuffs 5 causes the free side edge portions 5b of the cuff 5 to rise on the inner surface of the diaper 1. In the case of this diaper 1, the free side edge portions 5b of the cuffs 5 cooperate with the topsheet 2 to form a pair of pockets P opening inward laterally of the diaper 1.

The pair of leg-holes 12 and the waist-hole 13 are formed as free end portions of the respective tape fasteners 11 is anchored on the strip of target tape by means of pressure-sensitive adhesive (now shown) previously applied on inner surfaces of the respective free end portions. The sections of the transversely opposite side edges 1a lying in the crotch region 21 form the leg-holes 12, respectively, and the longitudinally opposite ends 1b form the waist-hole 13 as the diaper 1 is put on the wearer's body.

The crotch region 21 of the diaper 1 normally curved downward in a slackened state. From this state, the front and rear ends 6a, 6b; 7a, 7b of the first elastic member 6 and the second elastic members 7 are tensioned apart from each other, respectively, longitudinally of the diaper 1 as the diaper 1 is put on the wearer's body. Thus, a state in which the first elastic member 6 as well as the second elastic members 7 are stretched longitudinally of the diaper 1 between the front and rear waist regions 20, 22. The first elastic member 6 as well as the second elastic members 7 stretched in this manner generate longitudinally of the diaper 1 a tensile force higher than that before the diaper 1 is actually put on the wearer's body. The middle zone 4a and the side zones 4b of the core 4 lying in the crotch region 21 are supported by the middle zones 6c, 7c of the first and second elastic members 6, 7, respectively, so that the crotch region 21 having been heretofore in the slackened state may be lifted in the middle zone 4a and the side zones 4b of the core 4.

The middle zones 6c, 7c of the first and second elastic members 6, 7 are bonded neither to the backsheet 3 nor the core 4 and therefore stretching of these middle zones 6c, 7c of the elastic members 6, 7 are not restricted by the backsheet 3 and the core 4 at all. The middle zone 4a as well as the side zones 4b of the core 4 can be reliably supported by the middle zones 6c, 7c of these elastic members 6, 7 being adequately stretched.

Figure 3:
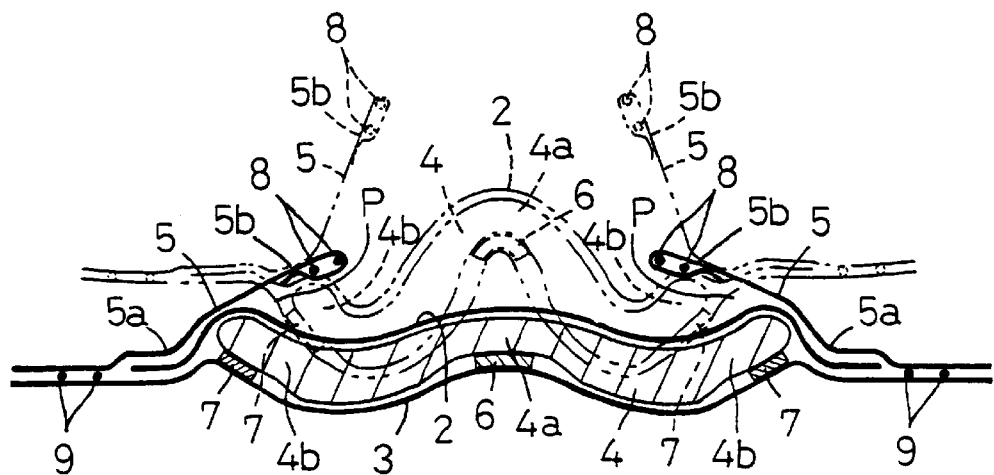
FIG. 3 is a sectional view taken along line B—B in FIG.

FIG. 3 is a sectional view taken along line B—B in FIG. 1 indicating the diaper 1 yet not put on the wearer's body by solid lines and indicating the diaper 1 put on the wearer's body by imaginary lines. A thickness of the core 4 is dimensioned so that the middle zone 4a in which the first elastic member 6 lies and the side zones 4b in which the second elastic members 7 lie are thinner than the remaining zone. Accordingly, a stiffness of the core 4 is lower in its middle zone 4a and side zones 4b than in the remaining zone and correspondingly said middle zone 4a and side zones 4b of the core 4 can be easily bent than the remaining zone.

With the diaper 1 yet not put on the wearer's body, the crotch region 21 extends horizontally without significantly slackening downwardly of the diaper 1. While such slight slack also is supported by the middle zones 6c, 7c of the first and second elastic members 6, 7, the middle zone 4a and the side zones 4b of the core 4 lying in the crotch region 21 are not lifted upwardly of the diaper 1 unless the diaper 1 is put on the wearer's body.

Upon being put on the wearer's body, the middle zone 4a and the side zones 4b of the core 4 lying in the crotch region 21 rise under the tensile force of the first and second elastic members 6, 7 stretched longitudinally of the diaper 1 and, in consequence, the crotch region 21 presents a W-shaped cross-section as indicated by imaginary lines in FIG. 3. The crotch region 21 bent in such W-shape substantially has its transverse dimension reduced. It is thus ensured to prevent the crotch region 21 from being irregularly deformed even if the crotch region 21 of the diaper 1 put on the wearer's body is tightly held between the wearer's thighs. Furthermore, even if the discharged body fluids flow on the topsheet from the middle zone 4a to the side zones 4b of the core 4, the side zones 4b of the core 4 are properly rising upwardly of the diaper 1 to form the barriers adapted to prevent the body fluids from leaking sideways.

The fixed side edge portions 5a of the respective cuffs 5 lie in the vicinity of the side zones 4b of the core lifted under the tensile force of the second elastic members 7. This arrangement ensures that the free side edge portions 5b of the cuffs 5 can be risen in postures substantially vertical or slightly slanted inward laterally of the diaper 1. In this way, the free side edge portions 5b of the cuffs 5 can be prevented from collapsing outwardly of the diaper 1 as the diaper 1 is put on the wearer's body. The free side edge portions 5b of the cuffs 5 are adapted to be risen around lines defined in the vicinity of the side zones 4b of the core 4. This means that the cuffs 5 will be able to fulfill their leak-barrier function even when the cuffs 5 are of an arrangement in which a distance between the fixed side edge portion 5a and the associated free side edge portion 5b is relatively small. In this diaper 1, not only the cuffs 5 but also the side zones 4b of the core 4 form the barriers so that the free side edge portions 5b of the cuffs 5 cooperate with the side zones 4b of the core 4 to improve the leak-barrier function of the diaper 1.

An alternative embodiment of the diaper 1 is also possible in which the front and rear ends 6a, 6b; 7a, 7b of the first and second elastic members 6, 7 are secured to the backsheet 3 with these elastic members 6, 7 being maintained under tension longitudinally of the diaper 1 while the middle zones 6c, 7c of these elastic members 6, 7 are intermittently secured to the backsheet 3. It is also possible to dimension a thickness of the core 4 in its middle and side zones 4a, 4b in which the first and second elastic members 6, 7 respectively lie to be same as that in the remaining zone.

The topsheet 2 may be formed by a liquid-pervious nonwoven fabric or a porous plastic film, preferably by a liquid-pervious hydrophilic sheet. The backsheet 3 may be formed by a hydrophobic nonwoven fabric, a liquid-impervious plastic film, a laminated sheet consisting of a hydrophobic nonwoven fabric and a plastic film, preferably by a breathable liquid-impervious sheet. The cuffs 5 may be formed by a hydrophobic nonwoven fabric, preferably by a breathable liquid-impervious sheet.

Nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. It is also possible to use a composite nonwoven fabric (SMS nonwoven fabric) comprising a melt blown nonwoven fabric having a high water resistance and two layers of spun bond nonwoven fabric having a high strength as well as a high flexibility covering both surfaces of the melt blown nonwoven fabric from above and below. This SMS nonwoven fabric is made by sandwiching the melt blown nonwoven fabric with the spun bond nonwoven fabric and then subjecting this assembly to a step of press to bond the melt blown nonwoven fabric and the spun bond nonwoven fabric to each other. Component fiber of the nonwoven fabric which can be used to exploit this invention may be selected from a group consisting of polyolefine-, polyester- and polyamide-fiber, and polyethylene/polypropylene or polyester conjugated fiber and the like.

The core 4 comprises a mixture of fluff pulp and high absorption polymer compressed to a desired thickness and entirely covered with a water-pervious sheet such as tissue paper (not shown). The first and second elastic members 6, 7 may be formed from tape-like, mesh-like or thread-like natural or synthetic rubber, stretchable nonwoven fabric tapes containing synthetic rubber as a principal ingredient, urethane foam tape or the like. Securing of the members constituting the diaper 1 may be carried out using suitable adhesive such as hot melt adhesive, pressure-sensitive adhesive or a heat-sealing technique.

What is claimed is:

1. A disposable diaper comprising:

a liquid-pervious topsheet;

a liquid-impervious backsheet;

a liquid-absorbent core disposed between said liquid-pervious topsheet and said liquid-impervious backsheet;

a front waist region;

a rear waist region;

a crotch region extending between said front and rear waist regions;

a first elastically stretchable member lying in a middle zone of said liquid-absorbent core and extending longitudinally of said diaper between said front and rear waist regions and being disposed between said liquid-impervious backsheet and said liquid-absorbent core and secured under tension to said liquid-impervious backsheet at portions of the first elastically stretchable member that are located between said liquid-impervious backsheet and said liquid-absorbent core; and a pair of second elastically stretchable members which lie in transversely opposite side zones of said liquid-absorbent core and extend longitudinally of said diaper between said front and rear waist regions and being disposed between said liquid-impervious backsheet and said liquid-absorbent core and secured under tension to said liquid-impervious backsheet at portions of the second elastically stretchable members that are located between said liquid-impervious backsheet and said liquid-absorbent core.

2. The diaper according to claim 1, wherein said first elastically stretchable member and each of said second elastically stretchable members are secured to said liquid-impervious backsheet at front end portions of said first elastically stretchable member and each of said second elastically stretchable members in said front waist region and at rear end portions of said first elastically stretchable member and each of said second elastically stretchable members in said rear waist region but not secured to said liquid-impervious backsheet at intermediate portions of said first elastically stretchable member and each of said second elastically stretchable members defined between said front and rear end portions of said first elastically stretchable member and each of said second elastically stretchable members.

3. The diaper according to claim 1, further including a pair of barrier cuffs extending longitudinally of said diaper in a vicinity of said side zones of said liquid-absorbent core which are normally biased so as to rise on an inner side of said diaper, each of said barrier cuffs having a fixed side edge portion bonded to the inner side of said diaper in a vicinity of the respective side zones of said liquid-absorbent core and extending longitudinally of said diaper, a free side edge portion extending from said fixed side edge portion inward laterally of said diaper, and longitudinally opposite fixed end portions lying in said front and rear waist regions and collapsed laterally of said diaper and bonded to said inner side of said diaper in a collapsed posture.

4. The diaper according to claim 1, wherein said liquid-absorbent core is thinner in said middle zone and said transversely opposite side zones than in remaining zones thereof.

* * * * *